United States Patent [19]
Huston et al.

[11] Patent Number: 5,984,972
[45] Date of Patent: Nov. 16, 1999

[54] PYLON ASSEMBLY FOR LEG PROSTHESIS

[75] Inventors: William Todd Huston; Scott Stromberg, both of Tulsa, Okla.

[73] Assignee: Amputee Solutions, Inc., Tulsa, Okla.

[21] Appl. No.: 08/933,449

[22] Filed: Sep. 18, 1997

[51] Int. Cl.$^6$ .................................................... A61F 2/60
[52] U.S. Cl. .................................................... 623/35; 623/27
[58] Field of Search ................................ 623/27, 35, 38, 623/50–52

[56] References Cited

U.S. PATENT DOCUMENTS

| | | | |
|---|---|---|---|
| 561,979 | 6/1896 | Erickson | 623/35 |
| 2,478,667 | 8/1949 | Shellhouse et al. | |
| 2,859,451 | 11/1958 | Mauch . | |
| 4,051,558 | 10/1977 | Vallotton . | |
| 4,513,457 | 4/1985 | Glabiszewski . | |
| 4,718,913 | 1/1988 | Voisin . | |
| 4,883,493 | 11/1989 | Martel et al. | 623/38 |
| 5,019,109 | 5/1991 | Voisin . | |
| 5,156,632 | 10/1992 | Wellerhaus . | |
| 5,158,570 | 10/1992 | Schey et al. | |
| 5,181,932 | 1/1993 | Phillips . | |
| 5,389,107 | 2/1995 | Nassar et al. | |
| 5,443,522 | 8/1995 | Hiemisch . | |
| 5,458,656 | 10/1995 | Phillips | 623/27 |
| 5,464,441 | 11/1995 | Phillips . | |
| 5,486,209 | 1/1996 | Phillips . | |
| 5,509,936 | 4/1996 | Rappoport et al. | |
| 5,514,185 | 5/1996 | Phillips . | |
| 5,514,186 | 5/1996 | Phillips . | |
| 5,545,234 | 8/1996 | Collier, Jr. | |
| 5,571,213 | 11/1996 | Allen . | |
| 5,702,488 | 12/1997 | Wood et al. | 623/27 |
| 5,728,175 | 3/1998 | Rincoe | 623/49 |

FOREIGN PATENT DOCUMENTS

| | | | |
|---|---|---|---|
| 5-309108 | 11/1993 | Japan | 623/50 |
| 605613 | 5/1978 | Russian Federation | 623/51 |
| 95/30391 | 11/1995 | WIPO | 623/43 |

*Primary Examiner*—David H. Willse
*Attorney, Agent, or Firm*—Scott R. Zingerman

[57] ABSTRACT

A pylon assembly for a leg prosthesis including an upper pylon, a lower pylon and a spring. A portion of both the upper pylon and the lower pylon are tubular. The spring is disposed between the upper pylon and the lower pylon inside the tubular portions. Upon assembly, the tubular portion of the lower pylon extends at least partially inside the tubular portion of the upper pylon with the spring extending from a plug inserted in the tubular portion of the lower pylon to a plug inserted in the tubular portion of the upper pylon. The spring biases the lower pylon away from the upper pylon. Compression and extension of the spring allows the lower pylon to reciprocate within the tubular portion of the upper pylon. This reciprocation allows the leg prosthesis to simulate the stride and cadence of a natural leg. In addition, a key may be inserted through the tubular portion of the upper pylon and extending into a key channel cut in the external circumference of the lower pylon. The width of the key channel being greater than the width of the key to allow the lower pylon to rotate within the upper pylon. A plurality of key channels may be cut around the circumference of the lower pylon (or interchangeable keys) each with a different width to allow variable amounts of rotation. This variable rotation allows proper rotation for a chosen activity but restricts undesirable excessive rotation of the lower pylon in relation to the upper pylon in order to simulate the lateral flexibility or rotation of a natural leg.

10 Claims, 3 Drawing Sheets

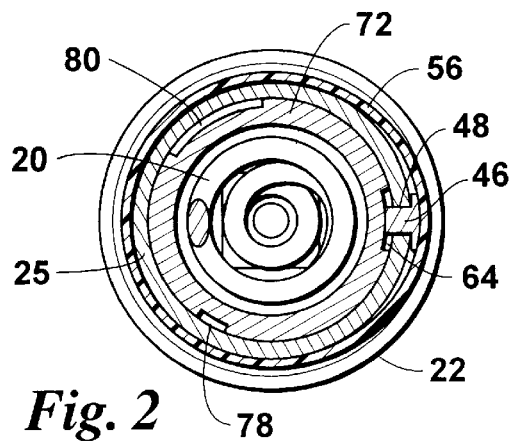
Fig. 2
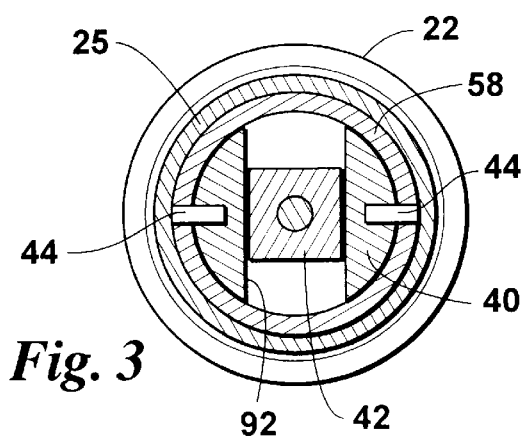
Fig. 3
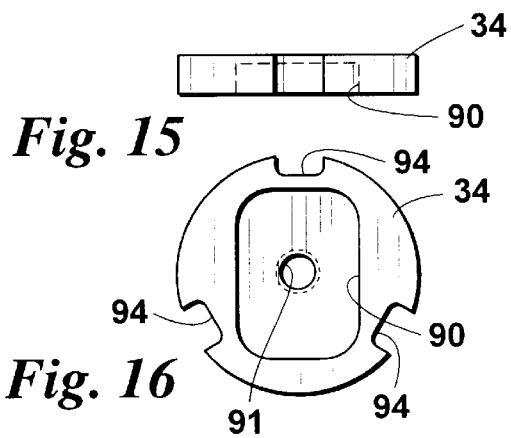
Fig. 15
Fig. 16
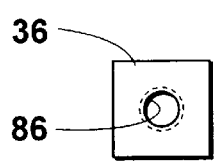
Fig. 14
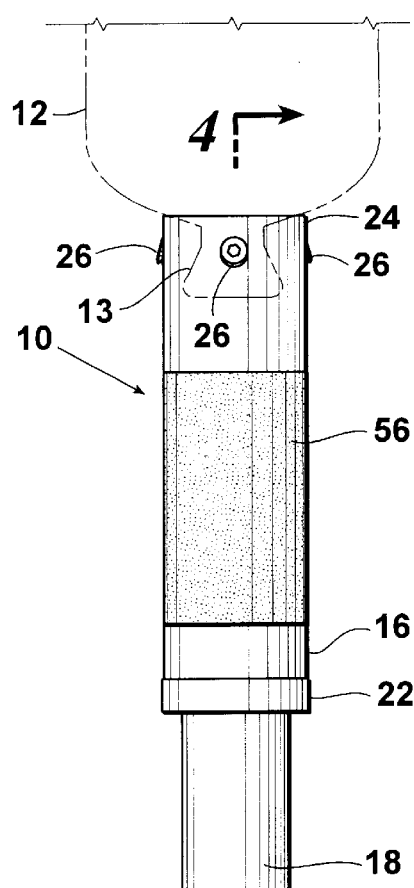
Fig. 1

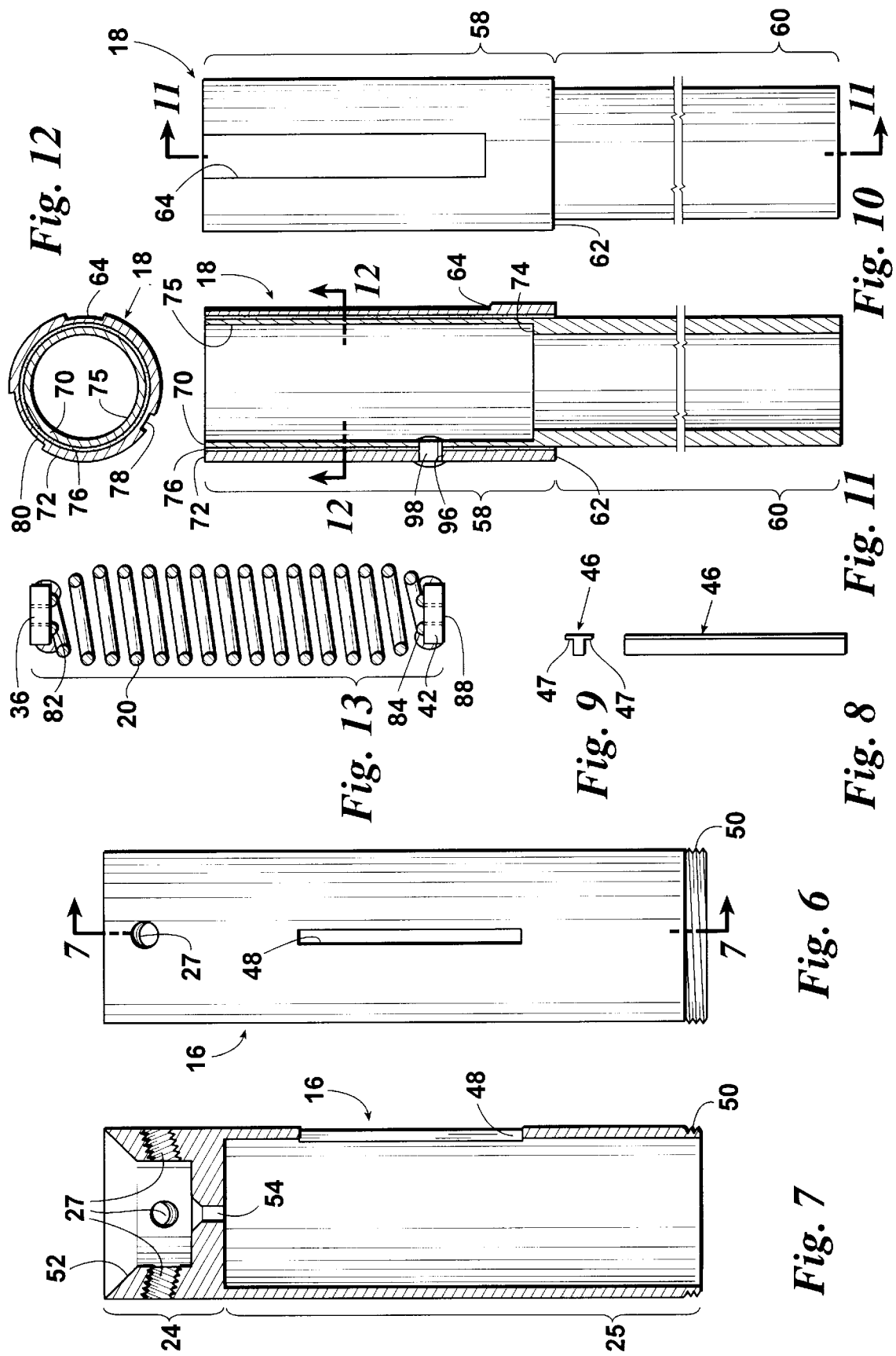

PYLON ASSEMBLY FOR LEG PROSTHESIS

BACKGROUND OF THE INVENTION

1. Field of the Invention

The present invention relates generally to the field of artificial limbs. More particularly, the present invention relates to leg prostheses including energy absorption and storage mechanisms.

2. General Background

Various types of leg prostheses are known which are designed to provide a support structure upon which the wearer can place his or her weight while standing or during the gait and/or stride associated with walking. The goal being to simulate the function and performance of the human leg. To accomplish this, leg prostheses generally include a mechanism for attachment to the limb of the wearer and an extension (pylon) mechanism either including or in combination with a foot prosthesis. The length and composition of the leg prosthesis being dependent upon the requirement of the wearer. The result being a rigid support mechanism simulating the structure of the human leg extending from the wearer's limb to the ground to provide the necessary support and balance for human activity. Such mechanisms are known in the industry as static leg prostheses.

Problems associated with static leg prostheses have been found with regard to their ability to simulate fluid stride cadence during walking, running, or other physical activities such as sports, exercise or labor. As a result, the ability of prosthesis wearers to participate in such activities has been historically limited.

In order for a static leg prosthesis to properly support a wearer, the prosthesis must be the same length as the other leg (or second prosthesis) of the wearer. However, while walking or running, the wearer must flex his or her hips to allow the prosthesis to swing forward for the next step without contacting the ground and also allow enough time for the prosthesis to swing forward in order to properly support the wearer on the next step.

An additional problem exists in that the gait/stride cadence of the wearer must be modified because of the inability of the static prosthesis to propel the body forward. This forward/upward force is a physiokinetic result of the flex of the calf muscles, ankle and foot of the human leg. Accordingly, a need exists for a pylon assembly for a leg prosthesis which reciprocates thereby varying the length of the prosthesis and provides alternating energy storage and release capability.

Another important limitation of leg prostheses presently available is the inability to provide for rotation of the wearer's limb with respect to the prosthetic foot along the length of the prosthesis pylon. Such rotation is a natural physiological characteristic of the human hip, thigh, knee and ankle necessary to successfully or competitively perform certain physical motions. In order to accurately simulate the human leg, a prosthesis must provide for this rotation.

In certain activities, such as a golf swing, It is necessary to provide rotation of the wearer's limb with respect to a fixed prosthetic foot. However, although rotation is necessary for many activities, unrestricted (free) rotation reduces the stability and/or controllability of the leg for other activities. A need, therefore also exists for a prosthesis pylon with provides rotation within preset limits which may be varied as required by the wearer or the activity.

SUMMARY OF THE INVENTION

The pylon assembly of the present invention includes an upper pylon, lower pylon, spring, and a collar. The upper pylon may be secured to a prosthetic socket and the lower pylon to a prosthetic foot to form a leg prosthesis.

The upper pylon includes means, such as an integral adapter segment for securing the upper pylon (and thereby the pylon assembly) to a prosthetic socket and a tubular segment to receive the spring. An upper plug assembly secures the spring within the tubular segment. The upper plug assembly includes an upper plug, an upper spring attachment plate welded to the top coil of the spring, and a screw. On assembly, the upper spring attachment plate welded to the top coil of the spring is press-fit into a channel within the upper plug and inserted within the tubular segment. The screw is then inserted through the adapter segment of the upper pylon into the tubular segment, upper plug and upper spring attachment plate, thereby securing the upper plug assembly within the tubular segment.

The tubular segment of the upper pylon also includes a key channel cut therein to receive a key. The key is shaped so as to fit into the key channel without passing therethrough, extends inside the tubular segment and is secured to the tubular segment. The key is designed to interact with a variable rotation channel in the lower pylon in order to provide restricted rotation ability to the pylon assembly that simulates the rotation ability of a natural leg.

The lower pylon includes a spring segment and an extension segment. The extension segment of the lower pylon also includes means for attachment to a prosthetic foot. Such means includes an adapter fixed to the extension segment which mates an adapter fixed to the prosthetic foot.

The spring segment is generally tubular so as to receive the spring opposite the upper pylon. The outer diameter of the spring segment of the lower pylon is less than the inside diameter of the tubular segment of the upper pylon so that the spring segment of the lower pylon may be inserted at least partially within the tubular segment of the upper pylon. A lower plug assembly secures the spring within the spring segment of the lower pylon.

When assembled, the top of the spring is secured to the upper pylon and extends at least partially inside the tubular segment, and the bottom of the spring is secured to the lower pylon and extends at least partially within the spring segment. The lower pylon reciprocates within the upper pylon and is biased from the upper pylon by the spring. This reciprocation of the lower pylon within the upper pylon as provided by the spring gives the pylon assembly energy storage and release ability which simulates a natural leg thereby providing a fluid (synchronous) stride/gate cadence to the wearer. The collar is threaded onto the upper pylon and helps retain the spring segment of the lower pylon within the tubular segment and the upper pylon.

The lower plug assembly of the lower pylon includes a lower spring attachment plate welded to the bottom coil of the spring and a lower plug. On assembly, the lower spring attachment plate welded onto the bottom coil of the spring is press fit into a channel cut into the lower plug. The lower plug assembly is then inserted into a machined-out portion of the spring segment of the lower pylon. A plurality of holes are then drilled through the outer circumference of the spring segment of the lower pylon and into the lower plug. Pins are inserted into these holes to secure the lower plug (and thereby the lower plug assembly) inside the machined-out portion of the spring segment. An adhesive, such as epoxy, may be applied between the lower plug and the machined-out portion to provide a chemical bond in addition to the mechanical bonds provided by the pins.

The outer diameter of the spring segment of the lower pylon is greater than the outer diameter of the extension segment. The lower pylon may be machined out of a solid mass of material or may be constructed from a tubular stock of material. In such construction, a tube is selected of a standard length and one end of this tube is machined out to form the machined-out portion of the spring segment. The machined-out portion having a greater inner diameter than the inner diameter of the extension segment with a ledge formed therebetween.

A small amount of material is then machined off of the outer circumference of the spring segment to received a braided sleeve. The sleeve is braided of material (such as carbon fiber) and is substantially the same length as the spring segment. The braided sleeve is impregnated with thermoplastic resin so as to become flexible when heated and then stretched and tightly slid over the tube of the spring segment. A bearing surface is then placed over the braided sleeve which may be secured by a rivet extending through the bearing surface, the braided sleeve and the tube. The hardened resin of the braided sleeve provides a chemical bond between the bearing surface and the tube. The spring segment of the lower pylon is thus formed.

Variable rotation channels are cut into the external circumference of the bearing surface. A plurality of such variable rotation channels may be cut in the external surface of the braided sleeve each having different widths. The variable rotation channels interact with the key extending into the tubular segment of the upper pylon to provide rotation to the pylon assembly.

The assembled lower pylon is inserted inside the tubular segment of the upper pylon so that the key fits into a variable rotation channel. The choice of variable rotation channel is made depending upon the amount of desired rotation of the pylon assembly. A variable rotation channel having a width greater than the width of the key will allow the lower pylon to rotate clockwise or counterclockwise within the limits of the width of the variable rotation channel. If a large amount of rotation is desired for a particular activity, a wide variable rotation channel is selected. Conversely, if no rotation is desired, a variable rotation channel having a width substantially the same as the width of the key is selected. Rotation ability of the lower pylon in relation to the upper pylon is thus provided.

As an alternative, a single variable rotation channel is contemplated having a width which matches the width of the key channel cut in the tubular segment of the upper pylon. Interchangeable keys having various widths could be substituted for the single key discussed above wherein the various keys provide alternate amounts of rotation of the lower pylon within the upper pylon.

It is thus an object of the present invention to provide a pylon assembly for a leg prosthesis which includes alternate energy storage and release capability upon reciprocation of lower pylon within an upper pylon.

It is a further object of the present invention to provide a pylon assembly for a leg prosthesis which allows for rotation of the lower pylon in relation to the upper pylon in order to simulate the rotation ability of a natural leg.

A still further object of the present invention is to provide a pylon assembly for a leg prosthesis which is light in weight yet durable for various physical activities. A yet further object of the present invention is to provide a pylon assembly for a leg prosthesis which is universal and capable of usage by persons of different sizes and weights which is not limited to location of amputation of the wearer's leg(s).

Other objects and advantages of the invention will become apparent upon reading the following detailed description and upon reference to the drawings.

BRIEF DESCRIPTION OF THE DRAWINGS

FIG. 1 is a side view of the pylon assembly for a leg prosthesis of the present invention attached to a prosthetic socket and prosthetic foot.

FIG. 2 is a view of the pylon assembly taken along line 2—2 of FIG. 4.

FIG. 3 is a view of the pylon assembly taken along line 3—3 of FIG. 4.

FIG. 6 is a side view of the upper pylon of the present invention including a key channel therein.

FIG. 7 is a cut-away view of the upper pylon taken along line 7—7 of FIG. 6.

FIG. 8 is a side view of the key which fits into the key channel of FIG. 6.

FIG. 9 is a end view of the key of FIG. 8.

FIG. 10 is a side view of the lower pylon of the present invention depicting a key channel cut therein.

FIG. 11 is a cut-away view of the lower pylon taken along line 11—11 of FIG. 10.

FIG. 12 is a cross-sectional view of the lower pylon taken along line 12—12 of FIG. 11 showing three key channels having various widths therein.

FIG. 13 is a side view of the spring assembly of the present invention including a spring with a spring attachment plate fixed on each end.

FIG. 14 is a plan view of a spring attachment plate.

FIG. 15 is a plan view of the upper plug including a spring attachment plate channel and a rotation lock therein.

FIG. 16 is a side view of the upper plug including a spring attachment plate channel therein.

DETAILED DESCRIPTION OF THE PREFERRED EMBODIMENT

Figure 4:
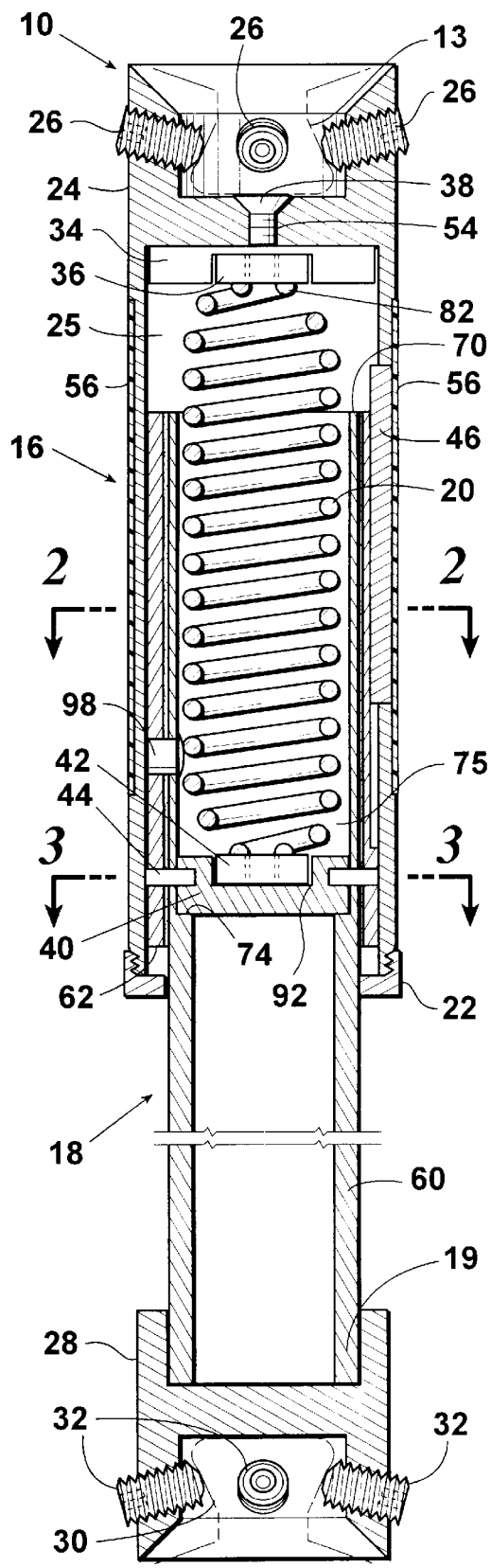
FIG. 4 is a view taken along line 4—4 of FIG. 1 showing the pylon assembly in the extended position.

The drawings illustrate an embodiment of this invention which may be broadly referred to as a pylon assembly for a prosthetic leg. Pylon assembly, generally 10 is shown in FIG. 1. Pylon assembly 10 may be secured to a prosthetic socket 12 (shown in phantom) and prosthetic foot 14 (shown in phantom) to form a leg prosthesis. Prosthetic sockets such as socket 12 are known in the art to receive the limb of a leg prosthesis wearer. Foot prostheses, such as foot prosthesis 14 are also known in the art to simulate a human foot.

Pylon assembly 10 broadly includes upper pylon 16, lower pylon 18, spring 20 (shown in FIG. 4), and collar 22. In the preferred embodiment, upper pylon 16 includes an integral female adapter segment 24 capable of receiving a male adapter 13 therein. Male adapter 13 is affixed to socket 12. Male adapter 13 is secured within adapter segment 24 by a plurality of set screws 26 threaded through adapter segment 24 and contacting male adapter 13. This attachment system can be seen in greater detail in FIGS. 4 and 5.

Prosthetic foot 14 is secured to lower pylon 18 of pylon assembly 10 using a similar system. A female adapter 28 is secured to lower pylon 18 in order to receive a male adapter 30. Male adapter 30 is attached to prosthetic foot 14 and extends therefrom. Male adapter 30 is secured within female adapter 28 by a plurality of set screws 32. In the preferred embodiment, adapter 28 is a four-hole adapter to receive four set screws 32 therein to secure male adapter 30, and thereby prosthetic foot 14 to lower pylon 18. This attachment mechanism can be seen in greater detail in FIGS. 4 and 5.

Now referring to FIG. 4, a view taken along line 4—4 of FIG. 1, the pylon assembly of the present invention can be seen in greater detail. Pylon assembly 10 broadly includes upper pylon 16, lower pylon 18, spring 20 and collar 22. Spring 20 extends between upper pylon 16 and lower pylon 18 in order to provide means to bias lower pylon 18 away from upper pylon 16. Spring 20 in interaction with upper pylon 16 and lower pylon 18 provides the alternating energy storage and release mechanism of my invention.

Spring 20 is secured inside upper pylon 16 by an upper plug assembly and inside lower pylon 18 by a lower plug assembly. The upper plug assembly includes upper plug 34, upper spring attachment plate 36 and screw 38. The lower plug assembly includes lower plug 40, lower spring attachment plate 42 and a plurality of pins 44. Pins 44 secure lower plug 40 inside lower pylon 18 (discussed below).

A key 46 is inserted through a key channel cut through the wall of upper pylon 16. A plurality of variable rotation channels are machined into the outer circumference of lower pylon 18 to receive key 46. Each variable rotation channel having a different width which is the same as or larger than the width of key 46. The interaction between key 46 and the variable rotation channels allow lower pylon 18 to rotate inside upper pylon 16 thereby providing means for rotation to pylon assembly 10 and the leg prosthesis.

Reference is next made to FIG. 6 which is a side view of upper pylon 16. In the preferred embodiment, upper pylon 16 is constructed of aluminum, however, it is understood that other materials such as titanium, composite material, or other materials known for their strength and light weight could be employed.

FIG. 6 depicts key channel 48 machined through the wall of upper pylon 16. A plurality of holes 27 are drilled and tapped through upper pylon 16 in order to receive set screws 26 (of FIG. 5). Threads 50 are machined onto upper pylon 16. Threads 50 mate the threads of collar 22 (of FIG. 5) so that collar 22 can be screwed onto upper pylon 16 to retain lower pylon 18 within upper pylon 16.

FIG. 7 is a cutaway view of upper pylon 16 taken along line 7—7 of FIG. 6. Upper pylon 16 includes adapter segment 24 and tubular segment 25. Adapter segment 24 further includes female adapter socket 52 capable of receiving a male adapter attached to the prosthetic socket as discussed above. Holes 27 are drilled and tapped in adapter segment 24 for receiving the set screws (26 of FIG. 4) in order to secure the male socket adapter within adapter segment 24. In the preferred embodiment, four such holes 27 are drilled in adapter segment 24, however, it is understood that a greater or fewer number of holes could be substituted as required. Adapter segment 24 also includes a screw aperture 54 drilled into tubular segment 25. Screw aperture 54 is machined so as to mate screw 38 in order to secure the upper plug assembly to upper pylon 16.

In the preferred embodiment, tubular segment 25 is substantially cylindrical along its length, annular in cross section and of an internal diameter to receive the upper plug assembly, spring 20 and lower pylon 16 therein. Key channel 48 as shown in FIG. 7 is cut through the wall of tubular segment 25 so that key channel 48 opens into tubular segment 25. As discussed above, threads 50 are machined into the terminal end of tubular segment 25. Threads 50 mate the threads of collar 22 so that collar 22 may be screwed onto tubular segment 25.

FIG. 8 is a side view of key 46. Key 46 is of the same dimensions as key channel 48 (of FIG. 6). On assembly, key 46 is secured in key channel 48.

In an alternate embodiment, a single variable rotation channel is contemplated having a width which matches the width of the key channel cut in the tubular segment of the upper pylon. Interchangeable keys having various widths could be substituted for the single key wherein the various interchangeable keys provide alternate amounts of rotation of the lower pylon within the upper pylon.

FIG. 9 is an end view of key 46. The width of key 46 is substantially the same as the width of key channel 48 (FIG. 6). Shoulders 47 of key 46 are wider than key channel 48 so that when key 46 is inserted into key channel 48, shoulders 47 abut upper pylon 16 thereby preventing key 46 from dropping inside tubular segment 25 of upper pylon 16.

As can be seen in FIG. 4, key 46 is longer than the thickness of the wall of tubular segment 25 so that a portion of key 46 extends inside tubular segment 25 (as can be seen in FIG. 4).

Upon assembly of upper pylon 16, key 46 is inserted into key channel 48 and secured therein by carbon fiber tape (or other suitable material) wrapped around the circumference of upper pylon 16. Alternate means of attachment such as a screw are also contemplated.

The section of carbon fiber tape securing key 46 into key channel 48 of upper pylon 16 can be seen in FIG. 1 denoted by the number 56. Taped portion 56 is of a slightly larger outer diameter than the outer diameter of tubular segment 25. Taped portion 56 can also be seen in cross section in FIG. 4.

Attention is next directed to FIG. 10, a side view of lower pylon 18. Lower pylon 18 includes a spring segment 58 and an extension segment 60. The outer diameter of spring segment 58 is greater than the outer diameter of extension segment 60. A shoulder 62 separates spring segment 58 from extension segment 60. FIG. 10 further depicts variable rotation channel 64 machined into the outer circumference of spring segment 58. Spring segment 58 serves to house spring 20 (as in FIG. 4) in combination with tubular segment 25, of upper pylon 16. The interrelation between spring segment 58, spring 20 and tubular segment 25 with key 46 therein provide the energy storage and release feature of the present invention.

Extension segment 60 serves as the pylon support structure of pylon assembly 10 to the prosthetic foot. As such, extension segment 60 is preferably rigid and constructed of lightweight material that is known for its strength and durability. The length of extension segment 60 will vary depending upon the height of the wearer and length of the wearer's limb as required to simulate the length of the wearer's natural leg. Pylon assembly 10 may be available in stock lengths wherein the terminal end of extension segment (19 of FIG. 4) is cut by a prosthetist to properly fit the wearer before adapter 28 is fixed to terminal end 19. Adapter 28 is then secured to terminal end 19. Once the proper length of extension segment 60 is properly established, adapter 28 is secured to terminal end 19 by suitable means known in the industry such as adhesive (epoxy), pins, rivets, set screws or the like. However, is has been found that adhesive (epoxy) is particularly suitable for this purpose.

Referring next to FIG. 11, a cut-away view taken line 11—11 of FIG. 10, lower pylon 18 is a composite of a tube 70, a braided sleeve 76, and a bearing surface 72 pressed over tube 70 in order to form spring segment 58.

Tube 70 is constructed of carbon fiber in the preferred embodiment, however, other suitable materials which are both strong and light weight could be substituted. Such materials may include, but are not limited to, aluminum, titanium and composite material. In the preferred embodiment tube 70 is cylindrical and tubular so as to keep the weight of the resulting pylon assembly at a minimum.

Lower pylon 18 may be machined out, or form molded of a solid stock of material or may be a composite constructed of different materials. This choice is related to the application and the relative costs of manufacture.

Lower pylon 18 (of composite construction) is constructed first by machining out the internal circumference of tube 70 so as to form a ledge 74 therein. This machined out portion of greater internal diameter forms the interior of spring segment 58 so as to receive a spring therein (such as spring 20 of FIG. 4). The width and length of machined out portion 75 within tube 70 is dependent upon the coil diameter and length of the spring to be inserted therein. The coil diameter and length of the spring is generally dependent upon the size and weight of the wearer. For example, an adult male would require a longer spring of larger coil diameter than a child. The length of the machined portion would typically range between ¾" to 2", however, it is understood that the length could be greater or smaller as required for a particular application. Ledge 74 is now capable of receiving a lower plug assembly as shall be discussed in greater detail below.

Figure 5:
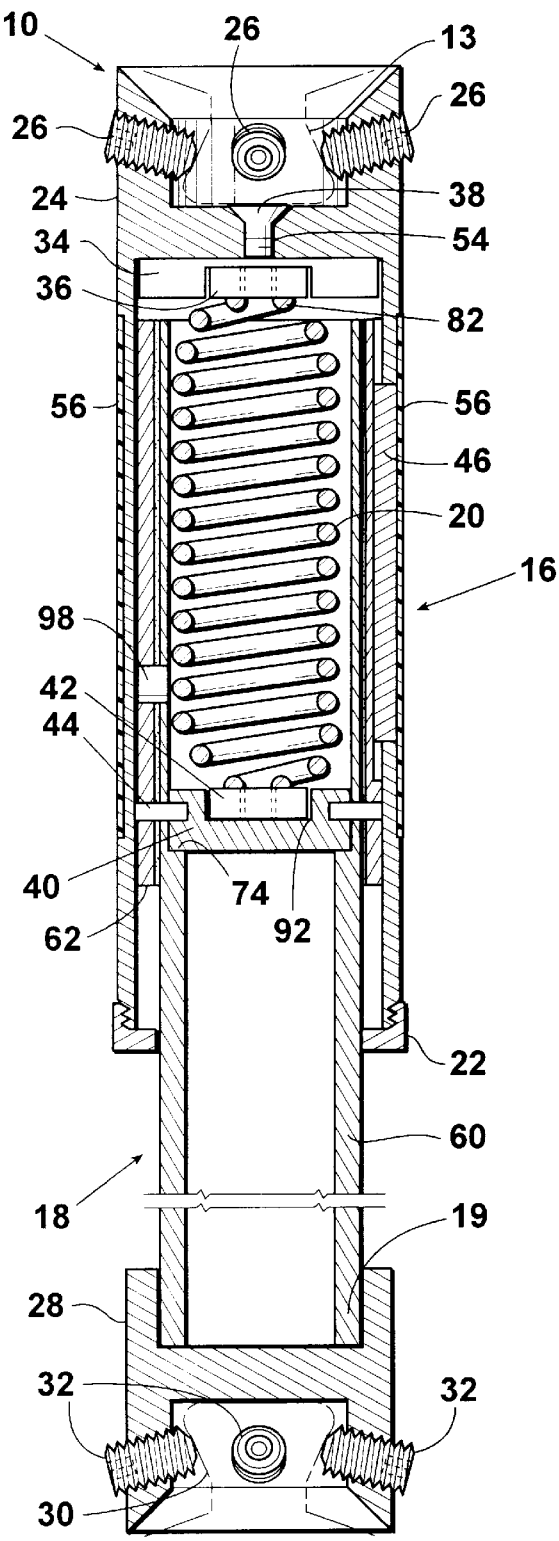
FIG. 5 depicts the pylon assembly of FIG. 4 in the compressed position.

The outer diameter of spring segment 58 is larger than the outer diameter of tube 70 for three main purposes. The first being that the larger outer diameter of spring segment 58 as compared to extension segment 60 is to create shoulder 62. As can be seen in FIGS. 4 and 5, shoulder 62 provides a stop surface against collar 22 when the pylon assembly 10 is in its extended position thereby protecting lower pylon 18 from separating from upper pylon 16.

The second purpose behind the increased outer diameter of spring segment 58 as compared to the outer diameter of extension segment 60 is to provide a wall in which a plurality of variable rotation channels (such as 64 in FIGS. 10 and 11) may be cut. As discussed in greater detail below, variable rotation channels are a part of the means for rotating the upper pylon within the lower pylon as may be required by certain physical activities.

The third purpose of the increased outer diameter of spring segment 58 is to provide increased wall thickness for additional strength while providing sufficient room for spring 20 to fit (as well as compress and expand) inside.

The outer diameter of spring segment 58 includes tube 70, a braided sleeve 76 of carbon fiber placed over tube 70, and a bearing surface pressed over the braided sleeve. Braided sleeve 76 is a thin sleeve of carbon fiber that is impregnated with thermoplastic resin. Braided sleeve 76 is cylindrical and has an internal diameter substantially the same as the external or outer diameter of tube 70 so that braided sleeve 76 fits tightly over tube 70. On installation, braided sleeve 76 is heated so that the thermoplastic resin softens and braided sleeve 76 becomes pliable. Braided sleeve 76 is then slid over tube 70 on spring segment 58. As an alternative, bearing surface 72 could be adhered directly to tube 70 using known commercial adhesives, such as epoxy, thereby eliminating braided sleeve 76.

Once braided sleeve 76 is installed onto tube 70, bearing surface 72 is pressed onto tube 70 over braided sleeve 76. The resin of braided sleeve 76 forms an adhesive bond with both tube 70 and the inner circumference of bearing surface 72. Bearing surface 72 is in the preferred embodiment constructed of ultra high molecular weight polyethylene. Other suitable materials include Teflon®, commercially available from DuPont, and Delryn®, manufactured by Phillips Petroleum Company and available commercially.

Bearing surface 72 is securely fixed to tube 70 once the resin impregnated in braided sleeve 76 cures by an adhesive bond and also a friction bond since bearing surface 72 is pressed tightly over braided sleeve 76 and tube 70. A rivet 98 is inserted in a hole 96 through bearing surface 72, braided sleeve 76, and tube 70 thereby securing the assembly. Spring segment 58 of lower pylon 18 is now assembled.

Referring next to FIG. 12, a plurality of variable rotation channels 64, 78 and 80 are machined into the outer circumference of bearing surface 72. Variable rotation channels 64, 78 and 80 receive key 46 (FIG. 4) and interact with key 46 so as to provide rotation of upper pylon 16 with respect to lower pylon 18. These variable rotation channels are each of different widths so as to provide numerous options for the wearer in order for the wearer to select a comfortable amount of rotation or the proper amount of rotation required by a specific activity. As can be seen in FIG. 12, variable rotation channel 80 is wider than variable rotation channel 64. As a result, variable rotation channel 80 would provide a larger arc of rotation than would variable rotation channel 64. Likewise, variable rotation channel 64 is wider than variable rotation channel 78 so that variable rotation channel 64 would provide a greater amount of rotation than would variable rotation channel 78. Variable rotation channel 78 is approximately the same width as key 46 of FIG. 9 so that when key 46 is positioned in variable rotation channel 78, little or no rotation would occur.

The interrelation between key 46 and the variable rotation channels in bearing surface 58 can also be seen with reference to FIG. 2. Referring to FIG. 2, a view of pylon assembly 10 taken along line 2—2 of FIG. 4, the interrelationship between key 46 and variable rotation channel 64 can readily be seen. In FIG. 2, a cross-sectional view, key 46 is shown extending through upper pylon 16, tubular segment 25 of upper pylon 16 and into variable rotation channel 64 of bearing surface 72. Since key 46 is fixed in key channel 48 by taped portion 56 (or other suitable means such as a screw or epoxy), key 46 will rotate uniformly with tubular segment 25 and upper pylon 16. Variable rotation channel 64 is wider than key 46 thereby allowing bearing surface 72 (and thereby lower pylon 18) to rotate in the clockwise or counterclockwise directions within the restricted limits of the width of variable rotation channel 64.

If key 46 is positioned (as will be discussed below) so as to be inserted in variable rotation channel 78, bearing surface 72 (and thereby lower pylon 18) will be immobilized from rotation either clockwise or counterclockwise because key 46 is the same width as variable rotation channel 78. Likewise, if key 46 is positioned to be inserted in variable rotation channel 80, bearing surface 72 (and thereby lower pylon 18) will be allowed a larger arc of rotation in the clockwise or counterclockwise direction within upper pylon 16 since variable rotation channel 80 is wider than variable rotation channel 64. However, key 46 and thereby upper pylon 16 will be restricted in its range of rotation within the limits of the width of variable rotation channel 80. Although the preferred embodiment of the present invention includes three variable rotation channels, each having different widths, it is understood that a smaller number of variable rotation channels are contemplated or a larger number of alternative width variable rotation channels limited only by the circumference of bearing surface 72.

Although not shown in the drawings relating to the preferred embodiment, a plurality of urethane (or other suitable material) bumpers could be adhered to the sides of variable rotation channels 64, and 80. These urethane bumpers would absorb shock and cushion the impact of key 46 against the sides of variable rotation channels 64 and 80. Key channel 78, being substantially the same width as key 46, would not require these bumpers. Alternatively, urethane bumpers could be adhered to the sides of key 46 in order to provide the same cushion effect.

Referring next to FIG. 13 which is a side view of spring 20 including upper and lower spring attachment plates secured thereto. As discussed above, the length and coil diameter of spring 20 may vary as is necessary to properly fit the wearer. In general, the spring will be selected so as to provide a deflection in the range of ½" to ¾", however, it is contemplated that springs allowing a greater or lesser amount of deflection could be substituted as may be required by a particular wearer or physical activity. A larger spring may require a larger pylon assembly to accommodate for a greater deflection, as for example to properly fit a heavier wearer or for a physical activity which may require increased energy storage and release capability of the pylon assembly such as basketball.

Both the top coil 82 and the bottom coil 84 of spring 20 are machined flat so that a spring attachment plate (36 and 42 respectively) can be fixed thereto. Spring attachment plates 36 and 42 are approximately ½" square and ¼" thick. Spring attachment plates 36 and 42 also include a hole drilled and tapped therethrough. By way of example, FIG. 14 depicts upper spring attachment plate 36 including hole 86 drilled and tapped therethrough. Hole 86 is drilled and tapped through upper spring attachment plate to receive a threaded screw (38 of FIG. 4) therethrough.

Attention next shall be directed to the upper plug assembly of FIG. 4 which includes upper plug 34, upper spring attachment plate 36 welded onto top coil 82 of spring 20, and screw 38. Upper spring attachment plate 36 is press fit into upper plug 34 and secured therein by screw 38 which extends into tubular segment 25 of upper pylon 16 through adapter segment 24 from adapter segment socket 52. It should be understood, however that other attachment mechanisms are contemplated in alternate embodiments. For example, hole 54 and screw 38 could be replaced with a plurality of holes drilled and tapped in the circumference of the tubular segment adjacent the adapter segment and into the upper plug. A screw could then be threaded into each such hole thereby securing the upper plug (and thereby the upper plug assembly) within the tubular segment.

Upper plug 34 is shown in greater detail in FIGS. 15 and 16. In FIG. 16, upper plug 34 is shown in plan view. Upper plug 34 includes a channel 90 cut therein. Channel 90 is substantially the same width as upper spring attachment plate 36 (FIG. 14) so that upper spring attachment plate 36 may be press fit therein. Upper plug 34 also includes a hole 91 drilled and tapped therein. Hole 91 is the same diameter and includes matching threads as hole 86 of upper spring attachment plate 36 so as to receive screw 38 (FIG. 4) therethrough.

The thickness of upper plug 34 is greater than the thickness of upper spring attachment plate 36. Channel 90 (shown in phantom in FIG. 15) is machined in upper plug 34 to a depth equal to the thickness of upper spring attachment plate 36 but does not extend through upper plug 34. In the preferred embodiment, the length of channel 90 is slightly longer than upper spring attachment plate 36 to facilitate aligning hole 86 of upper spring attachment plate 36 with hole 91 of upper plug 34 when upper spring attachment plate 36 is press fit into channel 90 of upper plug 34.

The outer circumference of upper plug 34 includes a plurality of rotation locks 94 notched therein. Rotation locks 94 allow upper plug 34 to to slide past key 46 when upper plug 34 is installed inside tubular segment 25 of upper pylon 16. Rotation locks 94 are, therefore, wider than key 46 and deep enough so as not to contact key 46 when upper plug 34 is inserted into tubular segment 25 past key 46. The number of rotation locks 94 cut into upper plug 34 will match the number of variable rotation channels 64 cut into bearing surface 72 of lower pylon 18. This is to allow upper plug 34 to pass key 46 when lower plug 18 is rotated to position key 46 into alternate variable rotation channels.

Upon installation (FIG. 4) the upper plug assembly is assembled with spring 20 welded to upper spring attachment plate 36 and fixed to upper plug 34 by press fitting upper spring attachment plate 36 into upper plug 34. The upper plug assembly is then inserted into tubular segment 25 past key 46 so that upper plug 34 is adjacent adapter segment 24 to be secured by screw 38. Assembly of pylon assembly 10 is discussed in greater detail below.

Attention next shall be directed to the lower plug assembly which includes lower plug 40, lower spring attachment plate 42, and spring 20 welded to lower spring attachment plate 42 at bottom coil 84. Lower plug 40 is substantially cylindrical like upper plug 34, however, lower plug 40 is smaller in diameter but greater in thickness than upper plug 34. Lower plug 40 is smaller in diameter than upper plug 34 so as to fit inside machined out portion 75 of lower pylon 18 against shoulder 74.

Lower plug 40, as with upper plug 34, includes a channel 92 machined therein to receive lower spring attachment plate 42. Lower spring attachment plate 42 is press fit into channel 92. Channel 92 is approximately the same depth as the thickness of lower spring attachment plate 42 so that lower spring attachment plate 42 fits flush within channel 92.

Lower plug 40 also differs from upper plug 34 in that lower plug 40 does not include rotation locks around its circumference since lower plug 40 does not come in contact with key 46. In the preferred embodiment, lower plug 40 does not include a hole drilled and tapped through its center like upper plug 34 since lower plug 40 is not fixed to lower pylon 18 by means of a screw attachment. However, it is understood that in an alternate embodiment, lower pylon 18 could be modified so that the lower plug attaches to lower pylon 18 by a threaded screw. Such an embodiment is contemplated where tube 70 of lower pylon 18 is a solid piece of material out of which spring segment 58 (including bearing surface 72 and machined out portion 75) and extension segment 60 are machined.

Lower plug 40 is greater in thickness than upper plug 34 in order to provide greater material mass to receive a plurality of pins 44 inserted through spring segment 58 of lower pylon 18. Pins 44 secure lower plug 40 to lower pylon 18 within machined out portion 75 adjacent shoulder 74.

Upon installation of the lower plug assembly, lower spring attachment plate 42 (welded to bottom coil 84 of spring 20) is press fit into lower plug 40. Lower plug 40 is then inserted into machined out portion 75 of lower pylon 18 adjacent shoulder 74. Two holes are then drilled through spring segment 58 positioned approximately 180° from each other around the circumference of spring segment 58. The holes are drilled through bearing surface 72, braided sleeve 76, tube 70 and into lower plug 40. The two holes are preferably positioned transverse to the length of channel 92 so as to avoid contact with channel 92. A pin 44 is then pressed into each hole flush with the circumference of bearing surface 72. Pins 44 fix the lower plug assembly securely within lower pylon 18.

FIG. 3 is a view taken along line 3—3 of FIG. 4 and shows in cross-section pins 44 extending through spring segment 58 and into lower plug 40. As can be seen, in the preferred embodiment, pins 44 do not extend into lower spring attachment plate 42 or channel 92. However, it is contemplated in an alternate embodiment pins 44 could extend into lower spring attachment plate 42 through channel 92. Also as can be seen in FIG. 3, pins 44 are flush with the outer circumference of spring segment 58 so as not to interfere with the reciprocation of spring segment 58 (and thereby lower pylon 18) within tubular segment 25 of upper pylon 16.

Pylon assembly 10 of FIG. 4 is assembled by first securing the lower plug assembly into machined out portion 75 adjacent shoulder 74 using pins 44 as discussed above. With lower spring attachment plate 42 press fit into lower plug 40 and bottom coil 84 welded to spring attachment plate 42, spring 20 is fixed inside machined out portion 75 of spring segment 58 so that top coil 82 of spring 20 welded to upper spring attachment plate 36 extends out of spring segment 58 opposite lower plug 40. The proper length of spring 20 extending from spring segment 58 will be greater than the maximum length of deflection required to properly support the wearer in an effort to prevent spring segment 58 from repeatedly contacting upper plug 34 as spring segment 58 reciprocates within tubular segment 25 as the wearer applies weight upon pylon assembly 10 during physical activity. This provides more fluid (smoother) motion to the wearer and reduces wear to the top of spring segment 58 and the bottom of upper plug 34. As such, the length of the portion of spring 20 extending from spring segment 58 will vary depending upon spring 20 as determined by the physical characteristics and preferences of the wearer. Upper spring attachment plate 36 extending from spring segment 58 is next press fit into upper plug 34.

Once the lower plug assembly is fixed inside lower pylon 18 and upper spring attachment plate 36 press fit into upper plug 34, spring segment 58 of lower pylon 18 is inserted inside tubular segment 25 of upper pylon 16. In doing so, lower pylon 18 is rotated so as to align key 46 with the selected variable rotation channel (such as 64 of FIG. 2) of spring segment 58. As discussed above, the rotation locks (94 of FIG. 16) are aligned with the variable rotation channels so that when spring segment 58 is inserted into tubular segment 25, rotation lock 94 allows upper plug 34 to slide past key 46 all the way to adapter segment 24.

Spring segment 58 is inserted into tubular segment 25 so that upper plug 34 contacts adapter segment 24 of upper pylon 16. Screw 38 is then inserted through screw aperture 54 in adapter segment 24 and threaded through upper plug 34 and into upper spring attachment plate 36. The upper plug assembly is now secured within tubular segment 25. Since upper plug 34 is fixed within tubular segment 25 adjacent adapter segment 24 and lower plug 40 is fixed inside machined out portion 75, spring segment 58 is now secured within tubular segment 25.

Once spring segment 58 is inserted inside tubular segment 25, collar 22 is threaded onto tubular segment 25. In the event that spring 20 becomes disconnected from either upper plug 34 or lower plug 40, collar 22 will prevent spring segment 58 from sliding out of tubular segment 25 as shoulder 62 of spring segment 58 contacts collar 22. Otherwise, shoulder 62 is not intended to contact collar 22. Pylon assembly 10 is now assembled.

Once pylon assembly 10 is assembled, spring segment 58 is free to reciprocate within tubular segment 25 both toward and away from adapter segment 24 as spring 20 compresses and expands (stores and releases energy). Likewise, spring segment 58 is free to rotate within tubular segment 25 within the restricted limits of rotation of key 46 in variable rotation channel 64 (FIG. 2). Energy storage and release as well as restricted rotation is thus provided by pylon assembly 10.

In the event that a different amount of rotation is desired by the wearer or required by a physical activity, pylon assembly 10 is easily disassembled and again reassembled with key 46 inserted in an alternate variable rotation channel on spring segment 58. Disassembly is accomplished by separation of adapter segment 24 from the prosthetic socket (12 of FIG. 1) unscrewing collar 22 from tubular segment 25, and removal of screw 38 from the upper plug assembly.

Removal of collar 22 and screw 38 will allow spring segment 58 (including the upper plug assembly) to be removed from tubular segment 25. Spring segment 58 is then rotated to align the alternate variable rotation channel (such as variable rotation channel 80 of FIG. 2) with key 46. Spring segment 58 is then reinserted inside tubular segment 25. Screw 38 and collar 22 are then reconnected once again securing spring segment 58 within tubular segment 25. This alternate selection allows spring segment 58 to rotate within tubular segment 25 within the limits of rotation of key 46 within variable rotation channel 80.

In the event that no rotation is desired, spring segment 68 is positioned so that key 46 is inserted within variable rotation channel 78 and spring segment 58 is secured within tubular segment 25 by screw 38 and collar 22. Since key 46 is the same width as variable rotation channel 78, spring segment 58 will be prevented from rotating within tubular segment 25. In this way selected limits of rotation are provided by pylon assembly 10.

Reference is next made to FIG. 5. FIG. 5 is the pylon assembly 10 of FIG. 4 wherein spring 20 is shown in the compressed position. In this position, such as when the wearer applies weight to pylon assembly 10, spring segment 58 of lower pylon 18 reciprocates within tubular segment 25 of upper pylon 16 toward adapter segment 24. Spring 20 stores energy in this compressed state. Spring 20 will release its stored energy when it returns to its extended (relaxed) state such as when the weight of the wearer shifts to the wearer's other leg. Spring 20 then biases (reciprocates) spring segment 58 of lower pylon 18 away from adapter segment 24 within tubular segment 25 thereby propelling the wearer forward and slightly upward. FIG. 4 depicts pylon assembly 10 with spring 20 in its extended state.

While the invention has been described with a certain degree of particularity, it is manifest that many changes may be made in the details of construction without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. A subcombination pylon assembly for use with a prosthetic socket and a prosthetic foot, said subcombination comprising:

an upper pylon having an adapter segment and a tubular segment wherein said adapter segment is configured to be attached to said socket;

a lower pylon including a spring segment and an extension segment wherein said spring segment is tubular and said extension segment is capable of attachment to the prosthetic foot;

a spring;

said spring extending between said lower pylon inside said spring segment and said upper pylon inside said tubular segment;

said spring being secured to said spring segment and said tubular segment thereby connecting said lower pylon to said upper pylon;

said upper pylon and said lower pylon each having a longitudinal axis;

said lower pylon being capable of reciprocation along its longitudinal axis relative to the longitudinal axis of said upper pylon.

2. The subcombination pylon assembly of claim 1, further including:

said tubular segment of said upper pylon having an inner diameter D;

said spring segment of said lower pylon having an outer diameter $D_1$;

said inner diameter D being larger than said outer diameter $D_1$;

said spring segment of said lower pylon being at least partially inserted inside said tubular segment of said upper pylon.

3. The subcombination pylon assembly of claim 2 further including:

a braided sleeve secured over said spring segment of said lower pylon;

a threaded collar:

a portion of said tubular segment of said upper pylon being threaded to receive said threaded collar.

4. A pylon assembly having a maximum length, comprising:

a cylindrical upper pylon having a longitudinal axis;

at least a portion of said upper pylon being tubular;

a cylindrical lower pylon having a longitudinal axis;

at least a portion of said lower pylon being tubular;

said tubular portion of said lower pylon being capable of reciprocation along its longitudinal axis in relation to the longitudinal axis of said tubular portion of said upper pylon;

means for biasing said lower pylon along its longitudinal axis away from said upper pylon and into a relationship corresponding to the maximum length of the pylon assembly;

said means for biasing being disposed between and within said tubular portion of said lower pylon and said tubular portion of said upper pylon;

said means for biasing being secured to said tubular portion of said lower pylon and said tubular portion of said upper pylon;

means for allowing said lower pylon to rotate within a restricted limit in relation to said upper pylon;

wherein said pylon assembly is configured to be a component of a prosthesis.

5. The pylon assembly of claim 4 wherein the means for biasing is a spring.

6. The pylon assembly of claim 5 wherein said tubular portion of said lower pylon extends at least partially within said tubular portion of said upper pylon.

7. The pylon assembly of claim 5 wherein said means for allowing said lower pylon to rotate in relation to said upper pylon further includes:

a variable rotation channel having a width cut in the circumference of said tubular portion of said lower pylon;

said tubular portion of said upper pylon including an internal circumference;

a key extending from the internal circumference of said tubular portion of said upper pylon;

said key extending into said variable rotation channel.

8. The pylon assembly of claim 7 wherein said key has a width substantially the same as the width of said variable rotation channel.

9. The pylon assembly of claim 7 wherein said key has a width which is less than the width of said variable rotation channel.

10. The pylon assembly of claim 7 wherein a plurality of variable rotation channels are cut in the circumference of said tubular portion of said lower pylon;

said key having a width;

each of said variable rotation channels having a different width;

the width of said variable rotation channels being at least as wide as the width of said key.

* * * * *